(12) United States Patent
Harari et al.

(10) Patent No.: US 9,895,519 B2
(45) Date of Patent: Feb. 20, 2018

(54) TREATMENT OF CAVITIES IN A HUMAN BODY

(71) Applicant: REGENTIS BIOMATERIALS LTD., Or Akiva (IL)

(72) Inventors: Boaz Harari, Ganey Tikva (IL); Amir Perle, Haifa (IL); Raz Simon, Kibbutz Alonim (IL)

(73) Assignee: REGENTIS BIOMATERIALS LTD., Or Akiva (IL)

( * ) Notice: Subject to any disclaimer, the term of this patent is extended or adjusted under 35 U.S.C. 154(b) by 558 days.

(21) Appl. No.: 14/507,246

(22) Filed: Oct. 6, 2014

(65) Prior Publication Data

US 2015/0100041 A1  Apr. 9, 2015

Related U.S. Application Data

(60) Provisional application No. 61/887,547, filed on Oct. 7, 2013, provisional application No. 61/931,149, filed on Jan. 24, 2014.

(51) Int. Cl.
*A61M 29/00* (2006.01)
*A61B 17/02* (2006.01)
(Continued)

(52) U.S. Cl.
CPC ......... *A61M 29/00* (2013.01); *A61B 17/0218* (2013.01); *A61B 17/8808* (2013.01);
(Continued)

(58) Field of Classification Search
CPC ........... A61F 2/30756; A61B 17/00234; A61B 17/1675; A61B 17/1682; A61B 17/1686; A61B 17/8808
See application file for complete search history.

(56) References Cited

U.S. PATENT DOCUMENTS 3,613,672 A * 10/1971 Schiff ................. A61M 1/1068
                                                         601/153
3,896,810 A *  7/1975 Akiyama ................. H04R 5/02
                                                         600/573
(Continued)

FOREIGN PATENT DOCUMENTS

DE      102009046728      5/2011
WO      1996/020749       7/1996

OTHER PUBLICATIONS

An Office Action dated Feb. 22, 2017, which issued during the prosecution of U.S. Appl. No. 14/679,309.
(Continued)

*Primary Examiner* — Scott Medway
(74) *Attorney, Agent, or Firm* — Dorsey & Whitney LLP

(57) ABSTRACT

Apparatus and methods are described, including apparatus for treating a cavity in a human body, the apparatus including a delivery tube. A bather device has a collapsed configuration and an expanded configuration, the barrier device moving from the collapsed configuration to the expanded configuration upon being deployed from the delivery tube. A pushing element, slidably disposed within a lumen of the delivery tube, is configured to deploy the barrier device from the delivery tube by pushing the bather device. One or more bather-deployment elements are coupled to the barrier device and to the pushing element, the bather-deployment elements being configured to conformingly contact the barrier device with tissue surrounding the cavity. Other applications are also described.

27 Claims, 15 Drawing Sheets

(51) Int. Cl.
*A61F 2/30* (2006.01)
*A61B 17/88* (2006.01)
*A61C 17/06* (2006.01)
*A61C 19/06* (2006.01)
*A61C 5/82* (2017.01)
*A61B 17/00* (2006.01)
*A61B 17/34* (2006.01)
*A61B 18/08* (2006.01)
*A61B 90/00* (2016.01)

(52) U.S. Cl.
CPC ............. *A61C 5/82* (2017.02); *A61C 17/043* (2013.01); *A61C 19/063* (2013.01); *A61F 2/30723* (2013.01); *A61B 17/3478* (2013.01); *A61B 18/08* (2013.01); *A61B 90/04* (2016.02); *A61B 2017/005* (2013.01); *A61B 2017/3488* (2013.01); *A61B 2090/0815* (2016.02); *A61B 2217/005* (2013.01)

(56) References Cited

U.S. PATENT DOCUMENTS

| | | | | |
|---|---|---|---|---|
| 4,048,990 A * | 9/1977 | Goetz | ............... | A61M 1/1062 601/153 |
| 4,508,107 A * | 4/1985 | Strom | ............... | A61H 23/04 601/107 |
| 4,909,789 A * | 3/1990 | Taguchi | ............... | A61B 17/0218 604/107 |
| 5,078,720 A * | 1/1992 | Burton | ............... | A61F 2/95 606/108 |
| 5,163,949 A * | 11/1992 | Bonutti | ............... | A61B 17/0218 606/192 |
| 5,256,132 A * | 10/1993 | Snyders | ............... | A61B 17/00234 600/16 |
| 5,336,252 A * | 8/1994 | Cohen | ............... | A61N 1/0587 606/129 |
| 5,484,391 A * | 1/1996 | Buckman, Jr. | ............... | A61M 1/1068 600/374 |
| 5,693,043 A | 12/1997 | Kittrell et al. | | |
| 5,795,353 A | 8/1998 | Felt | | |
| 6,129,662 A | 10/2000 | Li et al. | | |
| 6,200,280 B1 | 3/2001 | Brenneman et al. | | |
| 6,287,267 B1 | 9/2001 | Brenneman et al. | | |
| 6,319,224 B1 * | 11/2001 | Stout | ............... | A61M 5/30 604/140 |
| 6,406,444 B2 | 6/2002 | Brenneman et al. | | |
| 6,589,166 B2 * | 7/2003 | Knight | ............... | A61B 17/02 600/205 |
| 7,152,605 B2 | 12/2006 | KhairKhahan et al. | | |
| 7,179,224 B2 * | 2/2007 | Willis | ............... | A61B 17/30 600/201 |
| 7,291,146 B2 | 11/2007 | Steinke et al. | | |
| 7,597,704 B2 | 10/2009 | Frazier et al. | | |
| 7,720,533 B2 | 5/2010 | Behravesh et al. | | |
| 7,825,083 B2 | 11/2010 | Carter | | |
| 8,043,329 B2 | 10/2011 | KhairKhahan et al. | | |
| 8,052,750 B2 | 11/2011 | Tuval et al. | | |
| 8,109,962 B2 | 2/2012 | Pal | | |
| 8,137,354 B2 | 3/2012 | Stone | | |
| 8,157,805 B2 | 4/2012 | Re et al. | | |
| 8,221,310 B2 | 7/2012 | Saadat et al. | | |
| 8,323,309 B2 | 12/2012 | KhairKhahan et al. | | |
| 8,388,672 B2 | 3/2013 | KhairKhahan et al. | | |
| 8,777,956 B2 * | 7/2014 | Hoeppner | ............ | A61B 17/1604 606/167 |
| 9,492,291 B2 * | 11/2016 | Diwan | ............... | A61F 2/441 |
| 2002/0082220 A1 | 6/2002 | Hoemann et al. | | |
| 2004/0172055 A1 | 9/2004 | Huter et al. | | |
| 2005/0096502 A1 * | 5/2005 | Khalili | ............... | A61B 1/018 600/106 |
| 2005/0209602 A1 * | 9/2005 | Bowman | ............ | A61B 17/8805 606/90 |
| 2008/0058787 A1 | 3/2008 | Gertner | | |
| 2008/0125863 A1 | 5/2008 | McKay | | |
| 2008/0154233 A1 | 6/2008 | Yao et al. | | |
| 2011/0125159 A1 | 5/2011 | Hanson et al. | | |
| 2011/0125160 A1 | 5/2011 | Bagga et al. | | |
| 2013/0023731 A1 | 1/2013 | Saadat et al. | | |
| 2013/0110159 A1 * | 5/2013 | Litvack | ............... | A61B 17/0057 606/213 |
| 2015/0100041 A1 * | 4/2015 | Harari | ............... | A61M 29/00 604/513 |

OTHER PUBLICATIONS

An International Search Report and Written Opinion both dated Jan. 29, 2015, which issued during the prosecution of Applicant's PCT/IL2014/050876.
U.S. Appl. No. 61/887,547, filed Oct. 7, 2013.
U.S. Appl. No. 61/931,149, filed Jan. 24, 2014.
U.S. Appl. No. 14/679,309, Jun. 19, 2017, Office Action.

* cited by examiner

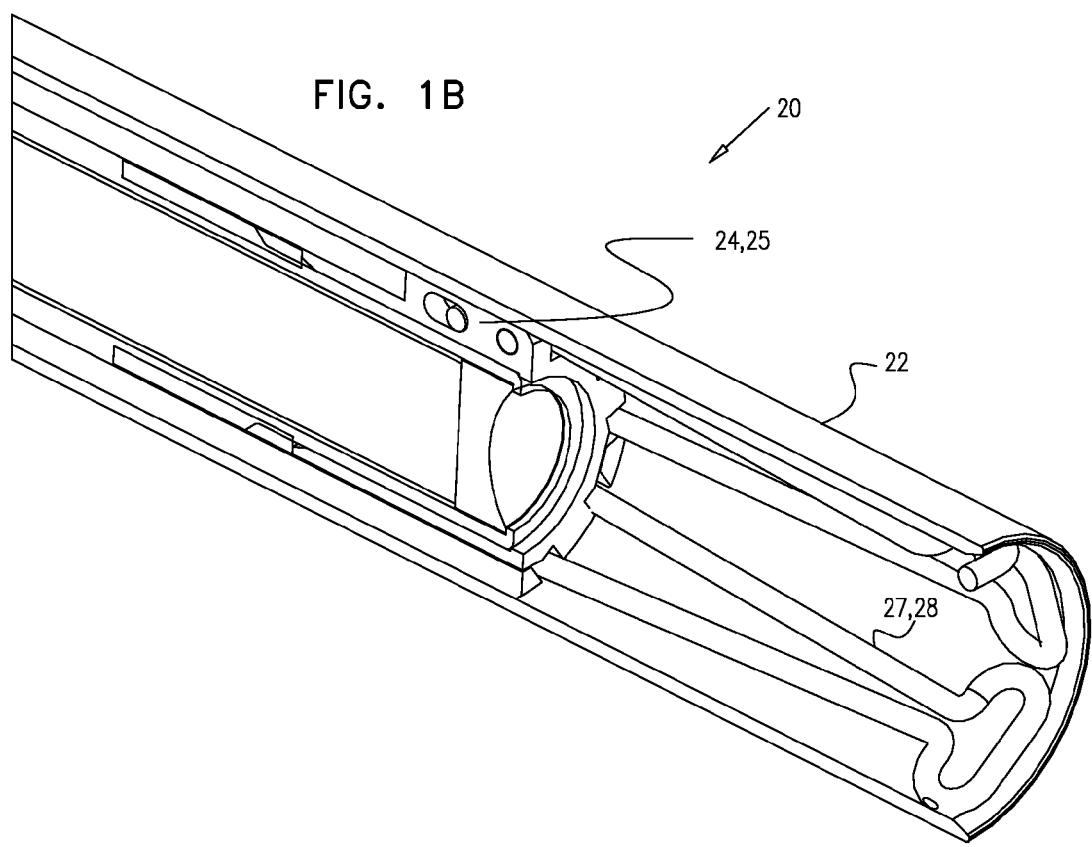

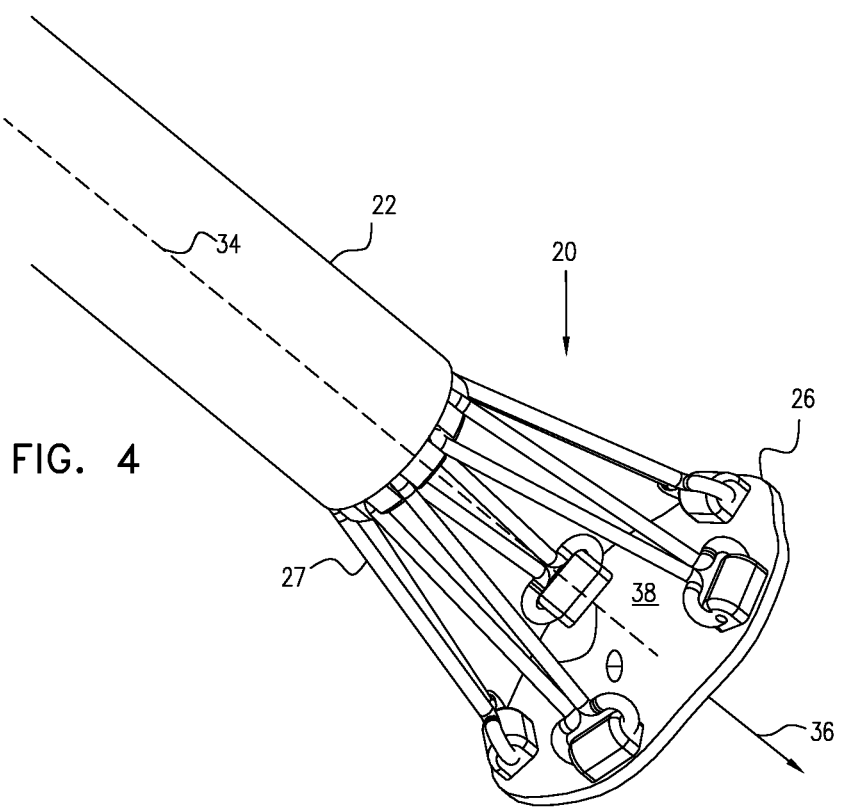

TREATMENT OF CAVITIES IN A HUMAN BODY

CROSS-REFERENCE TO RELATED APPLICATIONS

The present application claims the benefit of (i) U.S. Provisional Patent Application 61/887,547 to Harari, entitled "Apparatus for treatment of anatomical cavities", filed Oct. 7, 2013, and (ii) U.S. Provisional Patent Application 61/931,149 to Harari, entitled "Apparatus for treatment of cavities in a human body", filed Jan. 24, 2014. Each of the above-referenced applications is assigned to the assignee of the present invention and is incorporated herein by reference.

The present application is also related to a PCT Application entitled "Treatment Of Cavities In A Human Body," filed on even date herewith.

FIELD OF THE INVENTION

The present application is also related to PCT Application PCT/IL2014/050876, entitled "Treatment Of Cavities In A Human Body," filed on even date herewith (Oct. 6, 2014).

BACKGROUND

Treatment of cavities in a human body, e.g., repair of defects in cartilaginous or bone tissue, may be facilitated by use of a barrier device that isolates the region which is to be treated, in that isolation of the region allows for therapeutic agents to be applied effectively.

SUMMARY

Applications of the present invention address a number of challenges inherent in applying a barrier device to facilitate treatment of cavities in a human body. For example, the barrier device of some applications of the present invention conforms to tissue that surrounds the cavity, and is deliverable in a minimally-invasive manner. Furthermore, a mechanism that applies ultraviolet (UV) light may be integrated with the device, allowing for curing of applied therapeutic agents. Furthermore, the physician is typically able to view the cavity throughout the treatment procedure. Applications of the present invention may be applied to various types of cavities, including defects in cartilaginous tissue, bone tissue, and periodontal tissue.

There is therefore provided, in accordance with some applications of the present invention, apparatus for treating a cavity in a human body, the apparatus including:

a delivery tube;

a bather device having a collapsed configuration and an expanded configuration, the bather device moving from the collapsed configuration to the expanded configuration upon being deployed from the delivery tube;

a pushing element, slidably disposed within a lumen of the delivery tube, configured to deploy the bather device from the delivery tube by pushing the bather device; and one or more barrier-deployment elements coupled to the barrier device and to the pushing element, the batherdeployment elements being configured to conformingly contact the barrier device with tissue surrounding the cavity.

In some applications, the pushing element includes a tube.

In some applications, the one or more barrier-deployment elements include a plurality of legs.

In some applications, at least one of the legs is hingedly coupled to the pushing element.

In some applications, all of the legs are hingedly coupled to the pushing element.

In some applications, the apparatus further includes a hinge, and the at least one of the legs is hingedly coupled to the pushing element via the hinge.

In some applications, following deployment of the barrier device from the delivery tube, an angle between (a) each of the legs, and (b) a longitudinal axis of the delivery tube, is between 20 and 50 degrees, in the absence of any external forces applied to the apparatus.

In some applications, following deployment of the barrier device from the delivery tube, an angle between (a) each of the legs, and (b) a longitudinal axis of the delivery tube, is between 20 and 50 degrees, if a normal to a plane defined by the barrier device is parallel to the longitudinal axis of the delivery tube.

In some applications, the apparatus further includes a leg-control mechanism configured to facilitate control of a parameter selected from the group consisting of: (a) a position of at least one of the plurality of legs, with respect to the delivery tube, and (b) an orientation of at least one of the plurality of legs, with respect to the delivery tube.

In some applications, the one or more barrier-deployment elements include a spring.

In some applications, the one or more barrier-deployment elements include a shape-memory material.

In some applications, the one or more barrier-deployment elements include nitinol.

In some applications, a thickness of the barrier device is between 0.3 and 2 mm

In some applications, a surface area of the barrier device is between 1 and 10 cm2.

In some applications, the barrier device is configured to isolate the cavity from fluid between the barrier device and the pushing element, following deployment of the barrier device from the delivery tube.

In some applications, the barrier device is configured to trap fluid between the barrier device and the cavity, following deployment of the barrier device from the delivery tube.

In some applications, the barrier device includes a flexible sheet.

In some applications, the flexible sheet includes an elastomer.

In some applications, the elastomer includes a material selected from the group consisting of: polysiloxane, polyurethane, and polychloroprene.

In some applications, the apparatus further includes a suction tube shaped to define a suction tube lumen, the barrier device is shaped to define an opening therethrough, and the suction tube is coupled to the barrier device such that the suction tube lumen is in fluid communication with the opening.

In some applications, the barrier device is transparent to a type of light selected from the group consisting of: visible light, and ultraviolet A light.

In some applications, the barrier device is transparent to visible light and ultraviolet A light.

In some applications, the barrier device is translucent to a type of light selected from the group consisting of: visible light, and ultraviolet A light.

In some applications, the barrier device is translucent to visible light and ultraviolet A light.

In some applications, the barrier device is transparent to visible light and translucent to ultraviolet A light.

In some applications, the barrier device is translucent to visible light and transparent to ultraviolet A light.

In some applications, the apparatus further includes a scope configured to allow viewing of the cavity through the barrier device.

In some applications, the apparatus is for use with a light source, and the apparatus further includes a light guide, the light guide configured to guide light from the light source toward a distal end of the delivery tube.

In some applications, the apparatus is for use with an ultraviolet light source, and the light guide is configured to guide ultraviolet light from the ultraviolet light source toward the distal end of the delivery tube.

In some applications, the apparatus is for use with an ultraviolet light source, and the light guide is configured to guide ultraviolet light from the ultraviolet light source toward the distal end of the delivery tube.

In some applications, the apparatus is configured to allow for a continuum of angles between (a) a longitudinal axis of the delivery tube, and (b) a normal to a plane defined by the barrier device upon deployment thereof from the delivery tube, the continuum including an at least 40 degree continuum.

In some applications, the continuum of angles includes an at least 90 degree continuum, and the apparatus is configured to allow for the continuum of angles.

In some applications, the apparatus further includes a therapeutic agent delivery tube configured to deliver a therapeutic agent to the cavity.

In some applications, the apparatus is for use with a temperature regulator, and the apparatus further includes a heat-transfer element configured to be driven by the temperature regulator to transfer heat in a direction selected from the group consisting of: to the cavity, and from the cavity.

In some applications, a distal end of the heat-transfer element is coupled to the barrier device.

In some applications, the apparatus further includes a temperature sensor configured to sense a temperature of the cavity and communicate the sensed temperature to the temperature regulator.

In some applications, the temperature sensor is coupled to the barrier device.

In some applications, each one of the barrier-deployment elements is configured to pivot independently of each of the other barrier-deployment elements.

In some applications, at least one of the barrier-deployment elements includes a spring, including:

a first spring-arm that is pivotably coupled to the pushing element; and a second spring-arm that is pivotably coupled to the pushing element, a proximal end of the second spring-arm being more longitudinally moveable with respect to the pushing element than is a proximal end of the first spring-arm.

In some applications, a distal portion of the pushing element is shaped to define a channel, the proximal end of the second spring-arm being longitudinally moveable within the channel.

In some applications, a length of the channel is between 0.2 and 3 mm, and a width of the channel is between 0.2 and 2 mm.

In some applications, a ratio of a length of the channel to a width of the channel is between 1 and 5.

In some applications, the distal portion of the pushing element is shaped to define a hole, the first spring-arm is coupled to the pushing element by the proximal end of the first spring-arm fitting in the hole, and a ratio of a length of the channel to a diameter of the hole is between 1 and 5.

In some applications, the barrier device is configured to move from the collapsed configuration to the expanded configuration at least by the proximal end of the second spring-arm moving in a proximal direction.

There is further provided, in accordance with some applications of the present invention, a method for treating a cavity in a human body using a barrier device having a collapsed configuration and an expanded configuration, the method including:

deploying the barrier device from a delivery tube, using a pushing element slidably disposed within a lumen of the delivery tube, the barrier device moving from the collapsed configuration to the expanded configuration upon being deployed; and conformingly contacting the barrier device with tissue surrounding the cavity, using one or more barrier-deployment elements coupled to the barrier device and to the pushing element.

In some applications:

the cavity includes a defect selected from the group consisting of: a chondral defect, and an osteochondral defect, and conformingly contacting the barrier device with tissue surrounding the cavity includes conformingly contacting the barrier device with tissue surrounding the defect.

In some applications, the one or more barrier-deployment elements include a plurality of legs, and using the one or more barrier-deployment elements includes using the plurality of legs.

In some applications, the plurality of legs includes at least one leg that is hingedly coupled to the pushing element, and using the plurality of legs includes using the at least one leg.

In some applications, the at least one leg that is hingedly coupled to the pushing element includes all of the legs, and using the at least one leg includes using all of the legs.

In some applications, using the plurality of legs includes using a leg-control mechanism configured to facilitate control of a parameter selected from the group consisting of: (a) a position of at least one of the plurality of legs, with respect to the delivery tube, and (b) an orientation of at least one of the plurality of legs, with respect to the delivery tube.

In some applications, the one or more barrier-deployment elements include a spring, and using the one or more bather-deployment elements includes using the spring.

In some applications, conformingly contacting the barrier device with tissue surrounding the cavity includes isolating the cavity from fluid between the barrier device and the pushing element.

In some applications, the barrier device includes a flexible sheet, and deploying the barrier device includes deploying the flexible sheet.

In some applications, deploying the flexible sheet includes deploying a flexible sheet including a material selected from the group consisting of: silicone, and rubber.

In some applications, the method further includes suctioning fluid from the cavity using a suction tube.

In some applications:

the barrier device is shaped to define an opening therethrough, the suction tube is coupled to the barrier device such that a lumen of the suction tube is in fluid communication with the opening, and suctioning fluid from the cavity includes suctioning fluid through the opening.

In some applications, deploying the barrier device includes deploying a transparent barrier device.

In some applications, the method further includes viewing the cavity through the barrier device, using a scope.

In some applications, the method further includes guiding light from a light source toward a distal end of the delivery tube.

In some applications, guiding light includes guiding ultraviolet light toward the distal end of the delivery tube.

In some applications, the barrier device is transparent to ultraviolet light, and the method further includes passing ultraviolet light through the barrier device.

In some applications, the barrier device is translucent to ultraviolet light, and the method further includes passing ultraviolet light through the barrier device.

In some applications, the method further includes delivering a therapeutic agent to the cavity via a therapeutic agent delivery tube.

In some applications:

the bather device is shaped to define an opening therethrough, the therapeutic agent delivery tube is coupled to the barrier device such that a lumen of the therapeutic agent delivery tube lumen is in fluid communication with the opening, and delivering the therapeutic agent includes delivering the therapeutic agent through the opening.

In some applications, conformingly contacting the barrier device with tissue surrounding the cavity includes, following the deploying of the bather device, adjusting an angle between (a) a longitudinal axis of the delivery tube, and (b) a normal to a plane defined by the bather device upon deployment thereof from the delivery tube.

In some applications, deploying the barrier device includes deploying the bather device such that an angle between (a) a longitudinal axis of the delivery tube, and (b) a normal to a plane defined by the barrier device upon deployment thereof from the delivery tube, is greater than 5 degrees.

In some applications, the method further includes regulating a temperature of the cavity by using a temperature regulator to drive a heat-transfer element to transfer heat in a direction selected from the group consisting of: to the cavity, and from the cavity.

In some applications, the method further includes using a temperature sensor to sense a temperature of the cavity and communicate the sensed temperature to the temperature regulator, and regulating the temperature of the cavity includes regulating the temperature in response to the sensed temperature.

The present invention will be more fully understood from the following detailed description of embodiments thereof, taken together with the drawings, in which:

BRIEF DESCRIPTION OF THE DRAWINGS

FIGS. 1A-1C are schematic illustrations of apparatus for treating a cavity in a human body, in accordance with some applications of the present invention;

FIG. 4 is a schematic illustration of apparatus for treating a cavity in a human body, in accordance with some applications of the present invention;

DETAILED DESCRIPTION OF APPLICATIONS

Figure 1A:
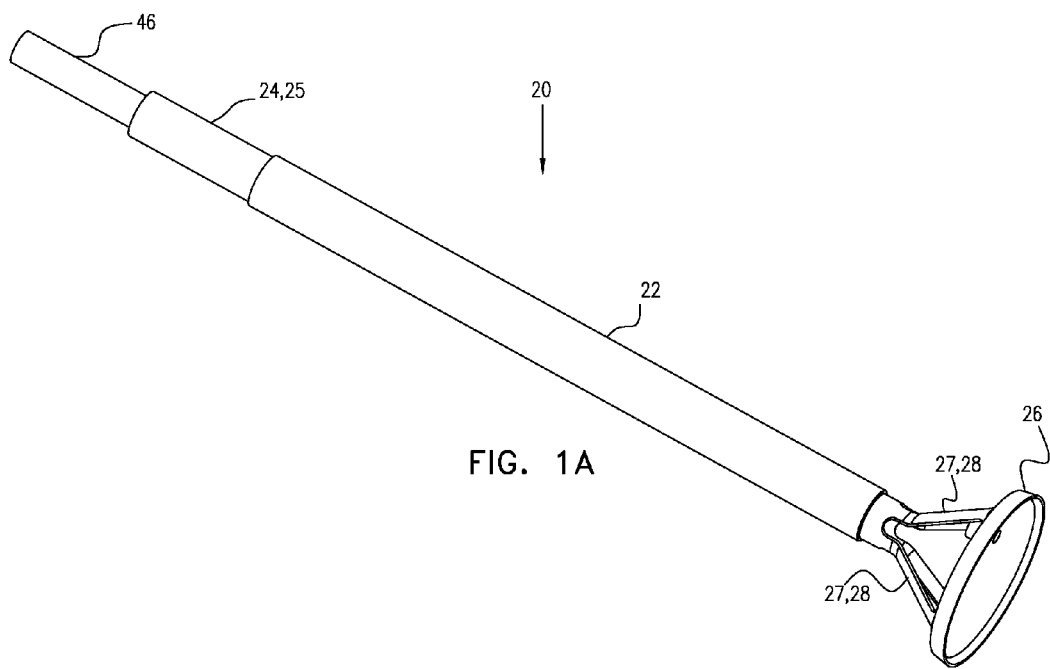
Figure 1C:
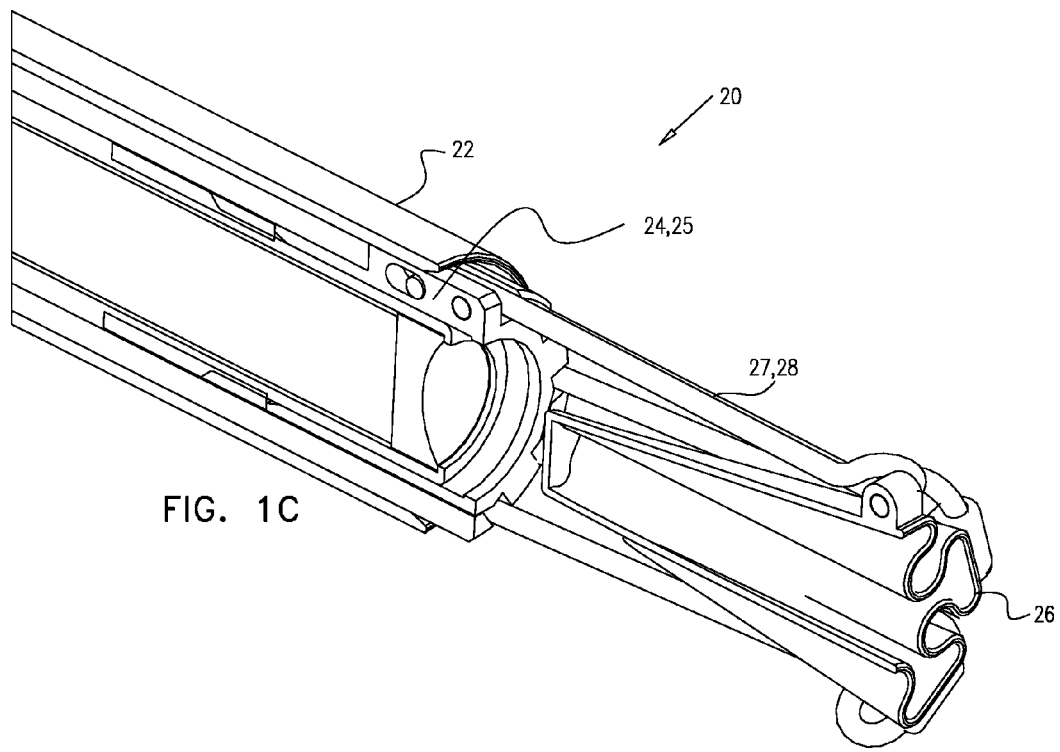

Reference is made to FIGS. 1A-C, which are schematic illustrations of apparatus 20 for treating a cavity in a human body, in accordance with some applications of the present invention. Apparatus 20 comprises a delivery tube 22, a pushing element 24, a barrier device 26, and one or more barrier-deployment elements 28. Barrier device 26 has a collapsed configuration and an expanded configuration. FIG. 1A shows the barrier device in its expanded configuration, while FIGS. 1B-C show the collapsed configuration. (FIG. 1B shows a cross-section of apparatus 20 in the collapsed configuration, wherein barrier device 26 is not shown, while FIG. 1C "peels away" a distal portion of delivery tube 22 and shows barrier device 26 in the collapsed configuration.) In the collapsed configuration, barrier device 26 and barrier-deployment elements 28 are typically inside delivery tube 22. The collapsed configuration of barrier device 26 facilitates the delivery of the barrier device in a minimally-invasive manner.

Figure 2:
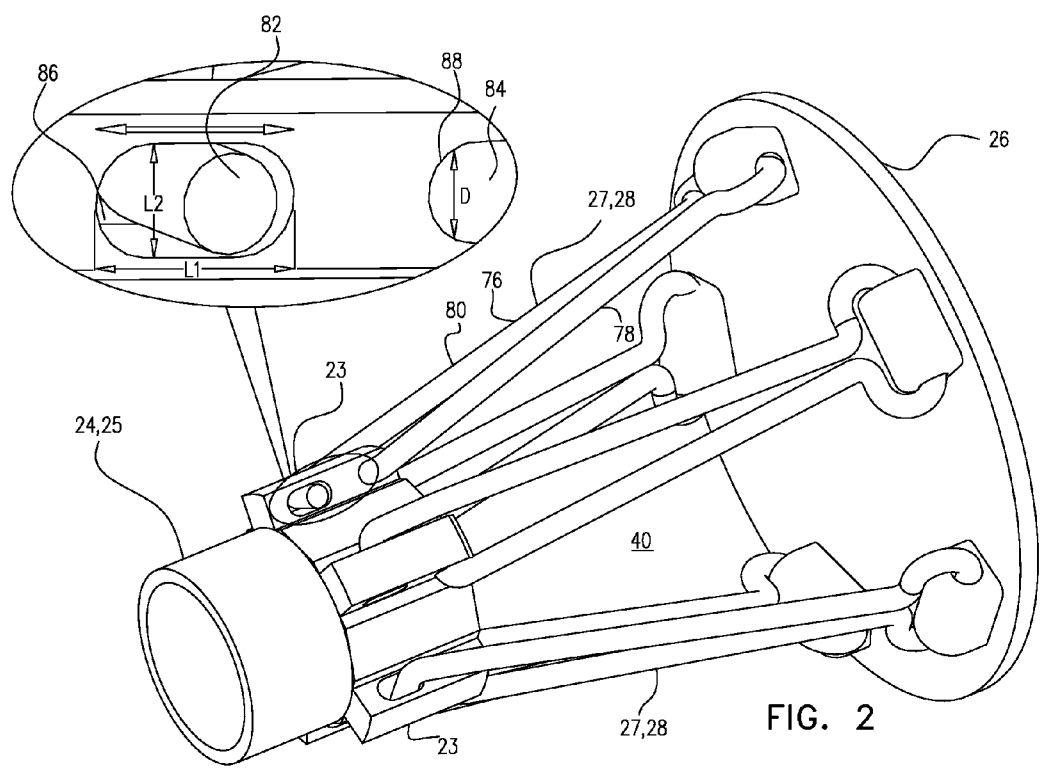
FIG. 2 is a schematic illustration of a coupling of a barrier device to a pushing element, in accordance with some applications of the present invention.

Reference is also made to FIG. 2, which is a schematic illustration of a coupling of a barrier device 26 to a pushing element 24, in accordance with some applications of the present invention. As shown in FIG. 2, barrier-deployment elements 28 are coupled to barrier device 26 and to pushing element 24. (FIG. 2 shows the distal end of pushing element 24.) For example, a distal portion of each of barrier-deployment elements 28 may be coupled to barrier device 26, e.g., near the perimeter of barrier device 26, and a proximal portion of each of barrier-deployment elements 28 may be coupled to pushing element 24. Pushing element 24 is slidably disposed within the lumen of delivery tube 22. As the distal end of pushing element 24 is moved toward the distal end of delivery tube 22, the pushing element pushes barrier device 26 in a distal direction. The pushing of barrier device 26 results in the barrier device being deployed from delivery tube 22, and the barrier device moving from the collapsed configuration to the expanded configuration. If the distal end of pushing element 24 is then moved toward the proximal end of delivery tube 22, barrier device 26 is retracted, moving from the expanded configuration to the collapsed configuration and entering delivery tube 22.

Although FIG. 1 shows barrier device 26 being deployed from the distal end of delivery tube 22, the scope of the present invention allows for barrier device 26 to be deployed from other orifices which delivery tube 22 may be shaped to define. In some applications, pushing element 24 comprises a tube 25, e.g., as shown in FIGS. 1A-C and FIG. 2.

Alternatively or additionally to moving pushing element 24, the barrier device may be deployed or retracted by moving delivery tube 22. For example, the barrier device may be deployed by sliding the delivery tube in a proximal direction. (While sliding the delivery tube, pushing element 24 may be used to apply a pushing force to the barrier device that facilitates the deployment of the barrier device by inhibiting the barrier device from moving proximally with the delivery tube.) In general, the deployment or retraction of the barrier device is effected by movement of the pushing element and/or delivery tube relative to one another. Typically, as depicted throughout the figures of the present application, each one of the barrier-deployment elements is configured to pivot independently of each of the other barrier-deployment elements.

In some applications, the one or more bather-deployment elements 28 comprise a plurality of legs 27, as shown in FIGS. 1A-C and FIG. 2. In some applications, as shown in FIG. 2, at least one of legs 27 is hingedly coupled to pushing element 24, in a manner that allows bather device 26 to move between the collapsed and expanded configurations. In some applications, as shown in FIG. 2, all of legs 27 are hingedly coupled to pushing element 24. In some applications, the apparatus further comprises a hinge 23, and at least one of legs 27 is hingedly coupled to pushing element 24 via hinge 23.

Reference is now specifically made to FIG. 2. In some applications, at least one of the barrier-deployment elements comprises a spring 76; for example, each of the barrier-deployment elements shown in FIG. 2 comprises a spring 76. (It is noted that spring 76 may also be referred to as a "leg," as described hereinabove.) Spring 76 comprises a first spring-arm 78 and a second spring-arm 80, each of which is pivotably coupled to the pushing element, e.g., via hinge 23. A proximal end 82 of second spring-arm 80 is more longitudinally moveable with respect to the pushing element than is a proximal end 84 of the first spring-arm. For example, as shown in FIG. 2, a distal portion of the pushing element may be shaped to define a channel 86, proximal end 82 of the second spring-arm being longitudinally moveable within channel 86, as depicted by the thick double-sided arrow. Typically, the distal portion of the pushing element is further shaped to define a hole 88, and the first spring-arm is coupled to the pushing element by proximal end 84 fitting in hole 88. Typically, a length L1 of the channel is between 0.2 and 3 mm, and/or a width L2 of the channel is between 0.2 and 2 mm. Alternatively or additionally, a ratio of L1 to L2 is between 1 and 5, and/or a ratio of L1 to a diameter D of the hole is between 1 and 5.

The two spring-arms of spring 76 have a tendency to move away from one another, if not inhibited from doing so. When contained within the delivery tube, second spring-arm 80 is inhibited from moving away from first spring-arm 78, such that proximal end 82 is in a relatively distal position, e.g., at the distal end of channel 86. Upon deployment of the barrier device, the proximal end of the second spring-arm moves in a proximal direction, e.g., toward the proximal end of channel 86, thus expanding the barrier device. In other words, spring 76 facilitates the deployment of the barrier device, in that the barrier device moves from the collapsed configuration to the expanded configuration at least by the proximal end of the second spring-arm moving in a proximal direction.

Figure 3A:
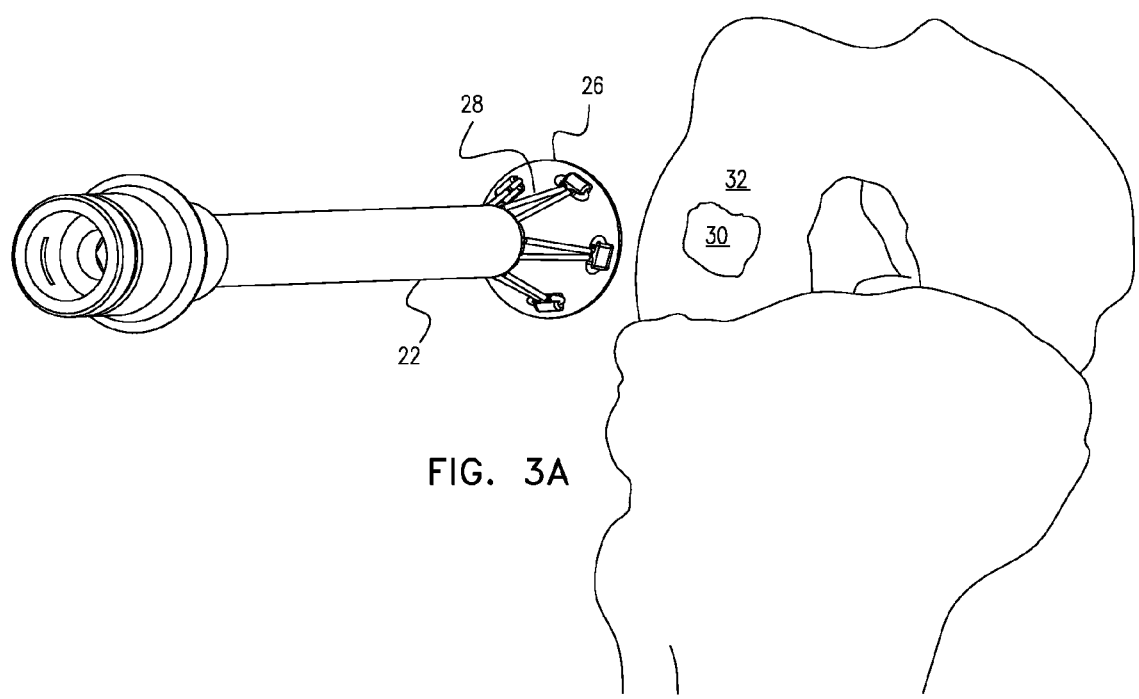
FIGS. 3A-3B are schematic illustrations of a barrier device conformingly contacting tissue, in accordance with some applications of the present invention.
Figure 3B:
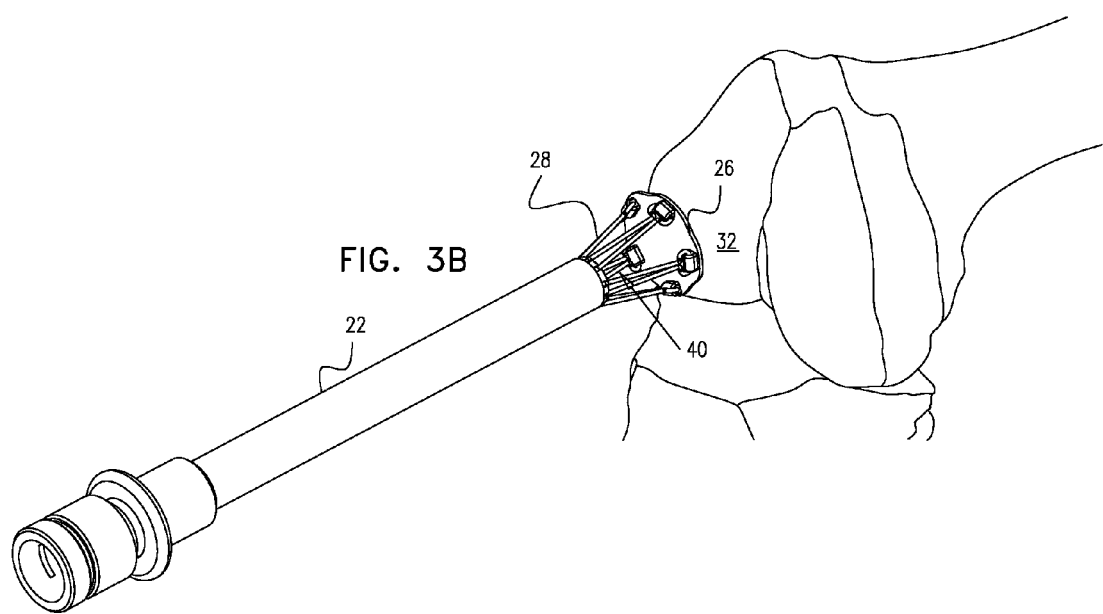

Reference is now made to FIGS. 3A-3B, which are schematic illustrations of a barrier device 26 conformingly contacting tissue 32, in accordance with some applications of the present invention. Barrier-deployment elements 28 are configured to conformingly contact barrier device 26 with tissue 32 surrounding a cavity 30 in a human body. Cavity 30 may include, for example, a chondral or osteochondral defect. The conformal contacting of barrier device 26 with tissue 32 facilitates treatment of cavity 30; for example, the conformal contacting of barrier device 26 may facilitate isolating cavity 30 from surrounding fluid and/or inhibiting a therapeutic agent applied to cavity 30 from leaving cavity 30. Thus, barrier device 26 typically isolates cavity 30 from fluid in a region 40 (FIG. 2) between the barrier device and the pushing element, following deployment of the barrier device from delivery tube 22. Similarly, barrier device 26 typically traps fluid (not shown) between the barrier device and cavity 30, following deployment of the barrier device from delivery tube 22.

Reference is now made to FIG. 4, which is a schematic illustration of apparatus 20 for treating a cavity in a human body, in accordance with some applications of the present invention. In some applications, following deployment of barrier device 26 from delivery tube 22, an angle theta between (a) each of legs 27, and (b) a longitudinal axis 34 of delivery tube 22, is at least 20 degrees and/or less than 50 degrees, in the absence of any external forces applied to apparatus 20 (e.g., if barrier device 26 is deployed in the air, not at the cavity). Alternatively or additionally, in some applications, following deployment of barrier device 26 from delivery tube 22, an angle between (a) each of legs 27, and (b) a longitudinal axis 34 of delivery tube 22, is at least 20 degrees and/or less than 50 degrees, if a normal 36 to a plane 38 defined by barrier device 26 is parallel to longitudinal axis 34.

Figure 5:
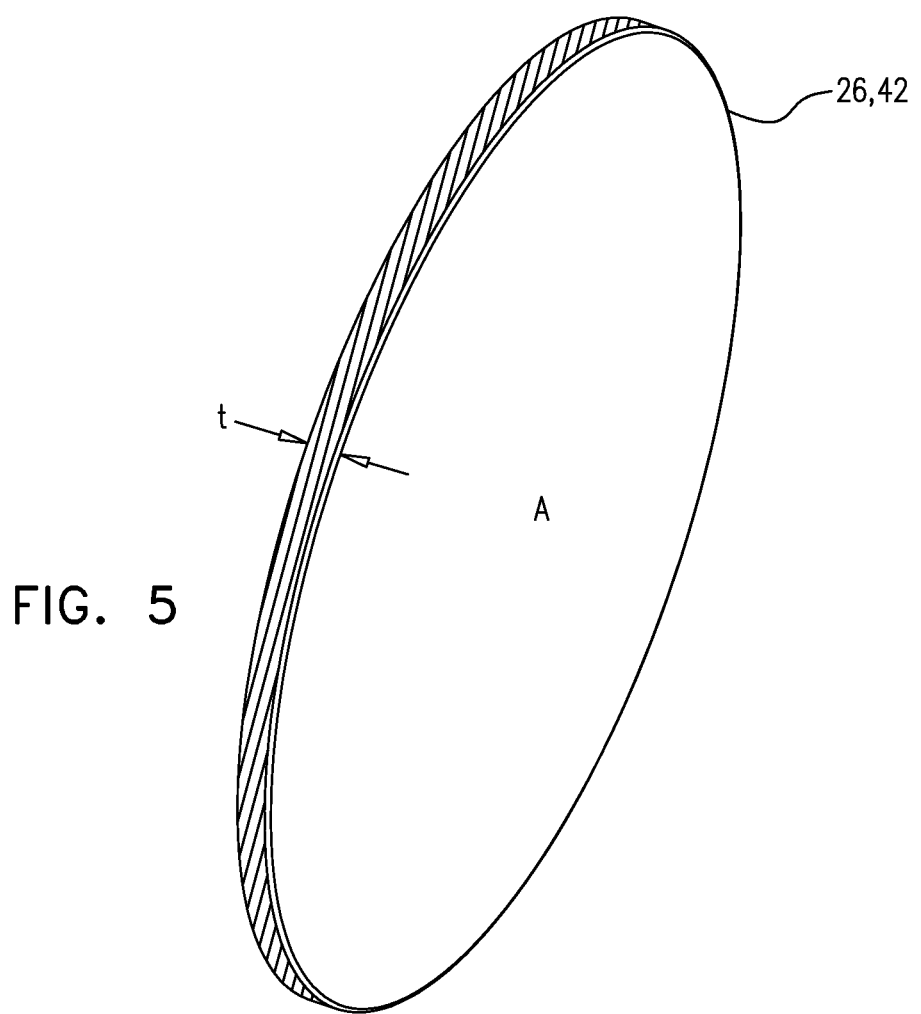
FIGS. 5-6 are schematic illustrations of a barrier device, in accordance with some applications of the present invention.
Figure 6:
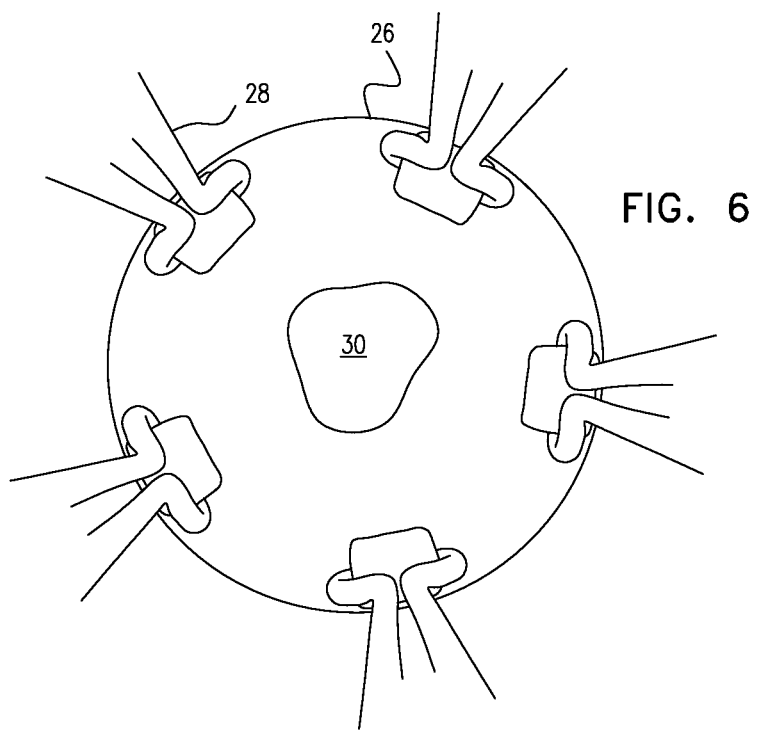

Reference is now made to FIGS. 5-6, which are schematic illustrations of a barrier device 26, in accordance with some applications of the present invention. In some applications, the thickness t of barrier device 26 is between 0.3 and 2 mm. In some applications, the surface area A of barrier device 26 is greater than 1 and/or less than 10 cm2. (For the sake of clarity, FIG. 5 shows barrier device 26 with an exaggerated thickness t, relative to surface area A.) In some applications, barrier device 26 comprises a flexible sheet 42. Flexible sheet 42 comprises, in some applications, an elastomer, which may comprise a material such as polysiloxane, polyurethane, and/or polychloroprene.

In some applications, as shown in FIG. 6, barrier device 26 is transparent or translucent to ultraviolet A (UV-A) light and/or visible light. In some applications, barrier device 26 is transparent to visible light and translucent to ultraviolet A light. In other applications, barrier device 26 is translucent to visible light and transparent to ultraviolet A light. The transparency or translucency of barrier device 26 facilitates application of UV light to cavity 30 and/or viewing of cavity 30 by a physician during the treatment procedure, as further described hereinbelow.

Figure 7:
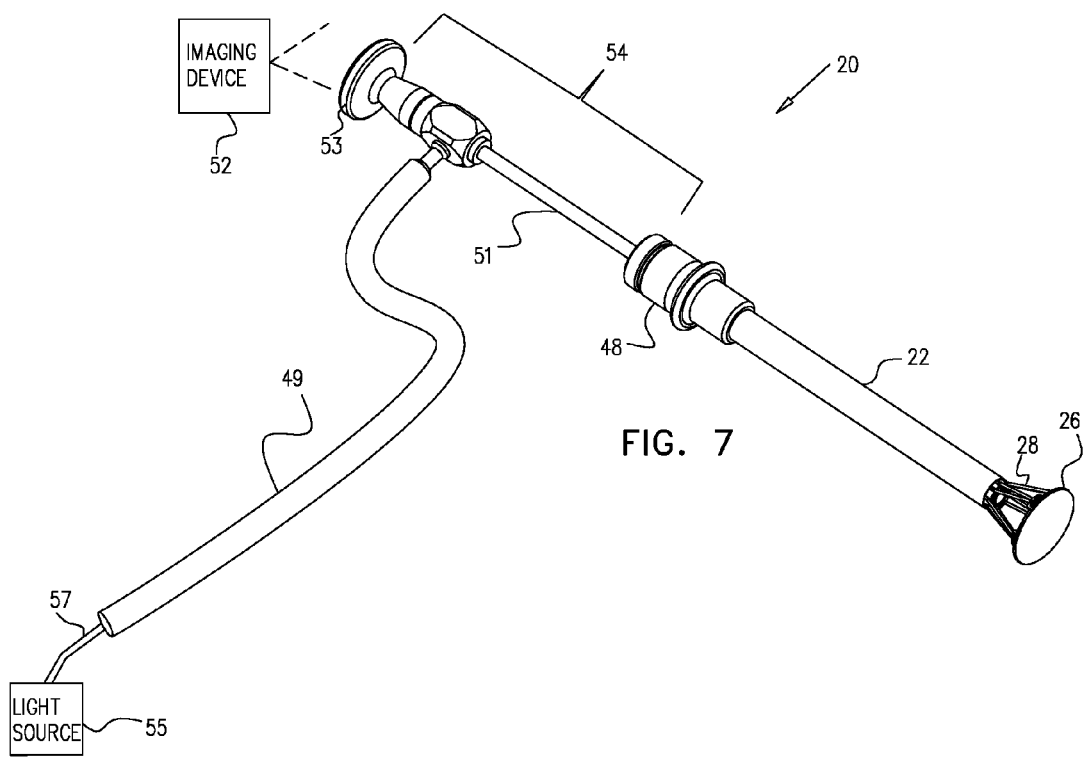
FIG. 7 is a schematic illustration of apparatus with a scope, in accordance with some applications of the present invention.

Reference is now made to FIG. 7, which is a schematic illustration of apparatus 20 with a scope 54, in accordance with some applications of the present invention. In some applications, apparatus 20 further comprises scope 54, configured to allow viewing of cavity 30 through barrier device 26. The proximal end 53 of scope 54 may be connected or juxtaposed to an imaging device 52, such as a camera, which generates an image for a physician to view during the treatment procedure.

In some applications, apparatus 20 is for use with a light source 55, and apparatus 20 further comprises a light guide 57 configured to guide light from light source 55 toward the distal end of delivery tube 22. Light guide 57 may comprise, for example, a fiber-optic cable. In some applications, light source 55 is a visible-light source, and light guide 57 is a visible-light guide. In these applications, light source 55 and light guide 57 are used in combination with scope 54; the guiding of visible light toward the distal end of delivery tube 22 facilitates the viewing of cavity 30 via scope 54. Light guide 57 typically runs through a light-guide-tube 49 and through the scope shaft 51 of scope 54, scope shaft 51 typically running to the distal end of delivery tube 22. Typically, an adaptor 48 holds scope 54 in place.

Figure 8:
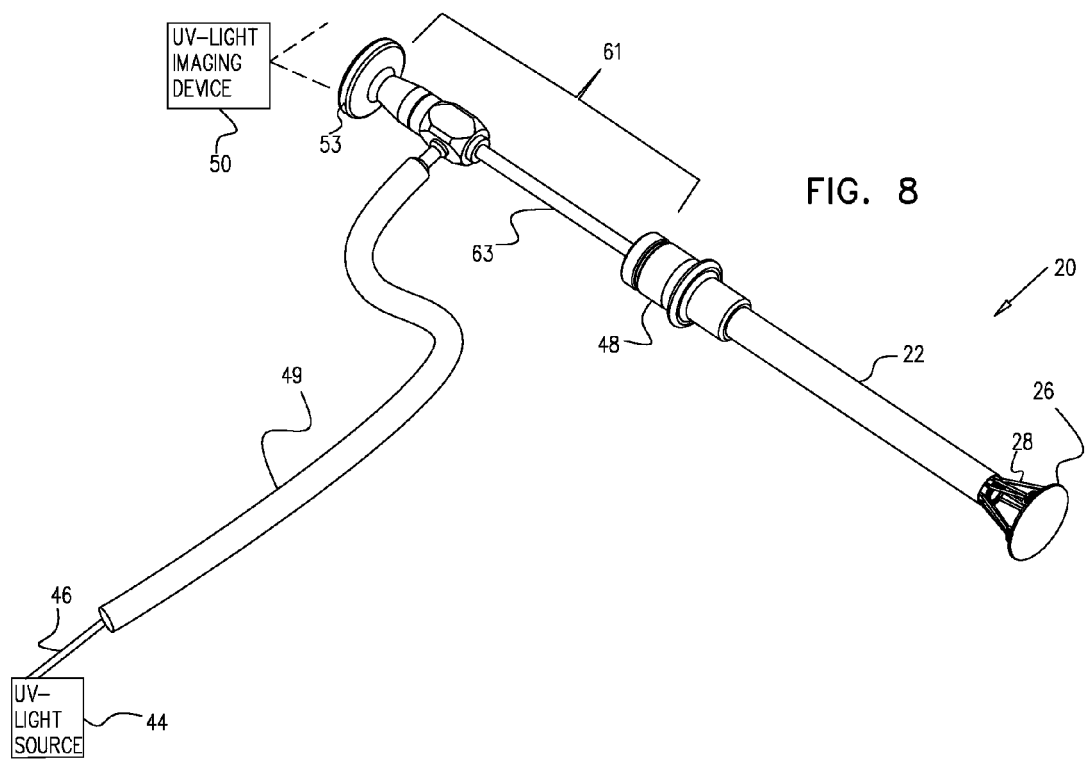
FIG. 8 is a schematic illustration of apparatus with an ultraviolet light source, in accordance with some applications of the present invention.

Reference is now made to FIG. 8, which is a schematic illustration of apparatus 20 with an ultraviolet light source 44, in accordance with some applications of the present invention. In some applications, apparatus 20 is for use with UV-light source 44, and apparatus 20 further comprises a light guide 46, light guide 46 being configured to guide UV light from UV-light source 44 toward the distal end of delivery tube 22. The UV light is guided by light guide 46 toward the distal end of delivery tube 22, and is emitted from delivery tube 22 toward cavity 30. In some applications, barrier device 26 is transparent or translucent to UV light, and the UV light is passed through barrier device 26 and into cavity 30. The application of UV light to cavity 30 facilitates the curing of therapeutic agents applied to the cavity. Light guide 46 may comprise, for example, a fiber-optic cable. UV-light source 44 and light guide 46 are typically used in combination with a UV scope 61. Light guide 46 typically runs through a light-guide-tube 49 and through the scope-shaft 63 of scope 61. Typically, adaptor 48 holds UV scope 61 place. In some applications, apparatus 20 is used with a UV-light imaging device 50, which generates an image for a physician to view during the treatment procedure.

Reference is made to FIGS. 7 and 8, which show apparatus for use in a typical treatment procedure, in accordance with some applications of the present invention. In a typical treatment procedure, the physician first deploys barrier device 26, and uses it to isolate cavity 30. Next, the physician attaches scope 54 to the rest of apparatus 20. Using light source 55 to illuminate cavity 30, the physician views cavity 30 through scope 54 and determines a treatment protocol. Next, the physician applies a therapeutic agent to cavity 30, as described hereinbelow with respect to FIG. 9. Next, the physician detaches scope 54 from the rest of apparatus 20, and attaches UV scope 61. Finally, using UV-light source 44, the physician cures the therapeutic agent.

Figure 9:
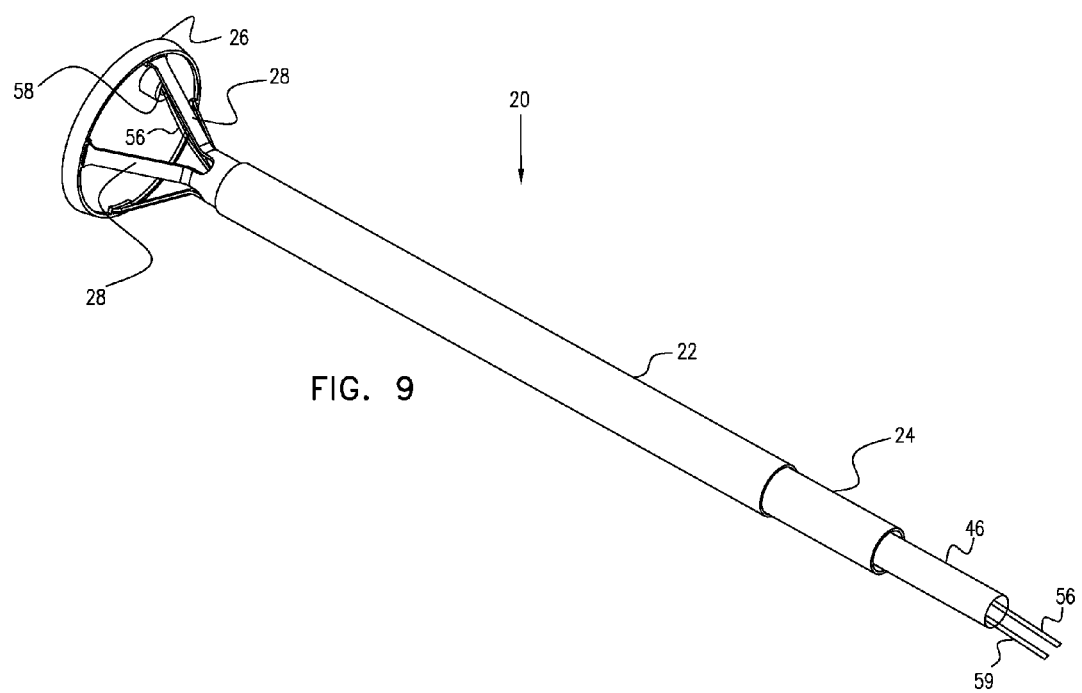
FIG. 9 is a schematic illustration of apparatus with tubes, in accordance with some applications of the present invention.

Reference is now made to FIG. 9, which is a schematic illustration of apparatus 20 with tubes, in accordance with some applications of the present invention. In some applications, apparatus 20 further comprises a suction tube 56 shaped to define a suction tube lumen. Bather device 26 is shaped to define an opening 58 therethrough, and suction tube 56 is coupled to the barrier device such that the suction tube lumen is in fluid communication with opening 58. In some applications, apparatus 20 alternatively or additionally comprises one or more therapeutic agent delivery tubes 59 configured to deliver a therapeutic agent to cavity 30. Therapeutic agent delivery tubes 59 may pass through delivery tube 22, as shown in FIG. 9, or may alternatively be disposed outside delivery tube 22, e.g., alongside delivery tube 22. In some applications, therapeutic agent delivery tubes 59 are configured to pass through opening 58 or through another opening which barrier device 26 is shaped to define. The use of more than one therapeutic agent delivery tube 59, e.g., two tubes 59, facilitates the application of agents that require in-situ mixing, such as certain types of sealant.

Figure 10:
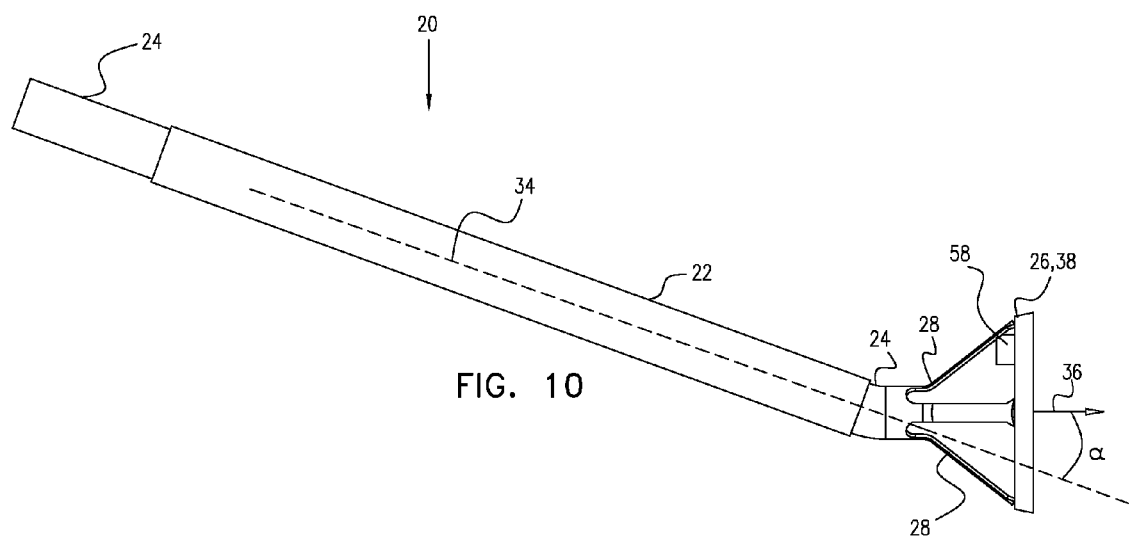
FIG. 10 is a schematic illustration of apparatus configured to allow for a continuum of angles, in accordance with some applications of the present invention.

Reference is now made to FIG. 10, which is a schematic illustration of apparatus 20 configured to allow for a continuum of angles, in accordance with some applications of the present invention. In some applications, apparatus 20 is configured to allow for a continuum of angles alpha between (a) a longitudinal axis 34 of delivery tube 22, and (b) a normal 36 to a plane 38 defined by barrier device 26 upon deployment thereof from delivery tube 22, the continuum including an at least 40 degree continuum. In some applications, the continuum includes an at least 90 degree continuum. The allowance for a continuum of angles facilitates the deployment of barrier device 26. For example, the barrier device may be deployed such that the angle is greater than 5 degrees, e.g., 15 degrees, thus facilitating the treatment of hard-to-reach areas. The allowance for a continuum of angles also facilitates the conformal contacting of the barrier device with tissue 32 (FIGS. 3A-3B), in that the angle may be adjusted to improve contact with the tissue.

Figure 11:
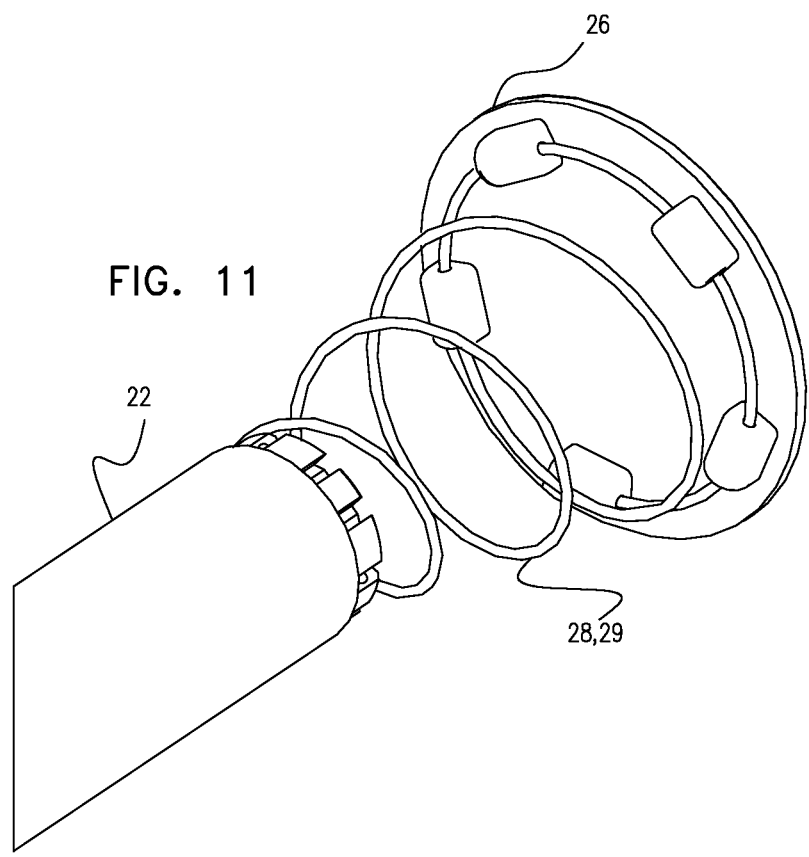
FIG. 11 is a schematic illustration of a spring element, in accordance with some applications of the present invention.

Reference is now made to FIG. 11, which is a schematic illustration of a spring element, in accordance with some applications of the present invention. In some applications, the one or more bather-deployment elements 28 comprise a spring 29. Spring 29 is configured to facilitate the deployment and retraction of barrier device 26, as has been described above with respect to legs 27, mutatis mutandis. In some applications, the one or more barrier-deployment elements 28 comprise a shape-memory material such as nitinol.

Figure 12:
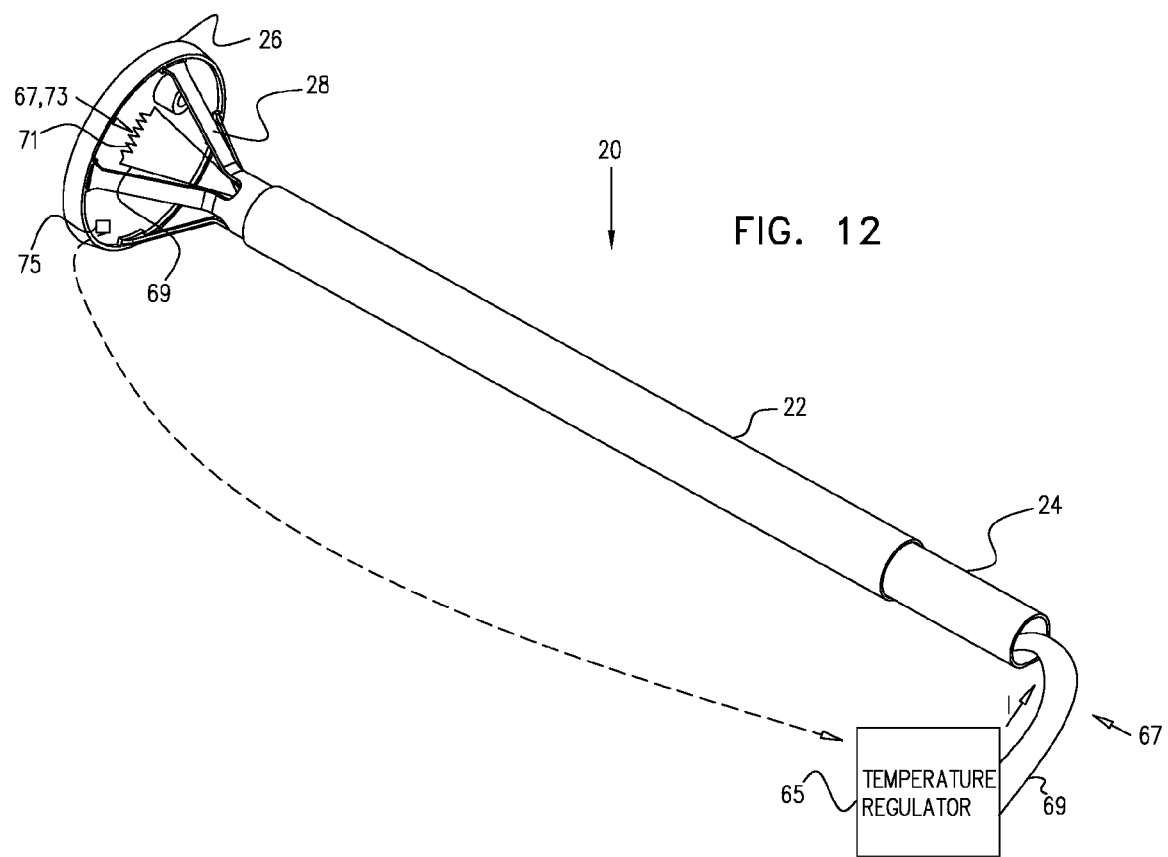
FIG. 12 is a schematic illustration of apparatus for use with a temperature regulator, in accordance with some applications of the present invention.

Reference is now made to FIG. 12, which is a schematic illustration of apparatus 20 for use with a temperature regulator 65, in accordance with some applications of the present invention. In some applications, apparatus 20 further comprises a heat-transfer element 67 configured to be driven by temperature regulator 65 to transfer heat to the cavity and/or from the cavity. For example, as shown in FIG. 12, heat-transfer element 67 may comprise a wire 69 and a resistor 71, the latter being disposed at a distal end 73 of the heat-transfer element. Current runs from temperature regulator 65 to resistor 71 through wire 69, through resistor 71, and back to temperature regulator 65 through wire 69. As the current passes through the resistor, heat is transferred to the cavity. The transfer of heat in this manner may facilitate treatment, such as by facilitating thermogelation of therapeutic agents applied to the cavity. Typically, distal end 73 of the heat-transfer element (e.g., resistor 71) is coupled to barrier device 26.

The scope of the present invention allows for heat-transfer element 67 to have various forms. For example, in some applications, heat may be transferred to and/or from the cavity via a fluid passing through a tube that runs between the temperature regulator and the cavity. Alternatively or additionally, for example, heat may be transferred to and/or from the cavity via a thermoelectric (Peltier) device.

Typically, apparatus 20 further comprises a temperature sensor 75 configured to sense a temperature of the cavity and communicate the sensed temperature (e.g., via wired or wireless communication) to the temperature regulator. The temperature regulator regulates the temperature of the cavity in response to the sensed temperature, by driving the heat-transfer element to transfer heat to and/or from the cavity. In some applications, e.g., as shown in FIG. 12, temperature sensor 75 is coupled to the barrier device. In other applications, temperature sensor 75 is disposed in other locations. For example, for applications in which the transfer of heat occurs via a fluid passing through a tube, as described above, the temperature sensor may be disposed proximate to or inside the temperature regulator.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for treating a cavity in a human body using a barrier device having a collapsed configuration and an expanded configuration, the method comprising:
    deploying the barrier device from a delivery tube, using a pushing element slidably disposed within a lumen of the delivery tube, the barrier device moving from the collapsed configuration to the expanded configuration upon being deployed; and
    conformingly contacting the barrier device with tissue surrounding the cavity, using a plurality of barrier-deployment elements coupled at respective distal ends thereof to the barrier device and to the pushing element,
    the cavity including at least one defect selected from the group consisting of: a chondral defect, and an osteochondral defect,
    wherein a first one of the barrier-deployment elements includes a spring, including:
        a first spring-arm that is pivotably coupled to the pushing element at a proximal end of the first spring-arm; and
        a second spring-arm that is pivotably coupled to the pushing element at a proximal end of the second spring-arm, wherein the proximal end of the second spring-arm is more longitudinally moveable with respect to the pushing element than is the proximal end of the first spring-arm.

2. The method according to claim 1, wherein conformingly contacting the barrier device with tissue surrounding the cavity comprises isolating the cavity from fluid between the barrier device and the pushing element.

3. The method according to claim 1, further comprising regulating a temperature of the cavity by using a temperature regulator to drive a heat-transfer element to transfer heat in a direction selected from the group consisting of: to the cavity, and from the cavity.

4. The method according to claim 1, wherein the barrier-deployment elements include a plurality of legs, and wherein using the barrier-deployment elements comprises using the plurality of legs.

5. The method according to claim 4, wherein the plurality of legs includes at least one leg that is hingedly coupled to the pushing element, and wherein using the plurality of legs comprises using the at least one leg.

6. The method according to claim 1, wherein the barrier device includes a flexible sheet, and wherein deploying the barrier device comprises deploying the flexible sheet.

7. The method according to claim 1, further comprising suctioning fluid from the cavity using a suction tube.

8. The method according to claim 7, wherein:
    the barrier device is shaped to define an opening therethrough,
    the suction tube is coupled to the barrier device such that a lumen of the suction tube is in fluid communication with the opening, and
    suctioning fluid from the cavity comprises suctioning fluid through the opening.

9. The method according to claim 1, wherein deploying the barrier device comprises deploying a transparent barrier device.

10. The method according to claim 9, further comprising viewing the cavity through the barrier device, using a scope.

11. The method according to claim 1, further comprising guiding light from a light source toward a distal end of the delivery tube.

12. The method according to claim 11, wherein guiding light comprises guiding ultraviolet light toward the distal end of the delivery tube.

13. The method according to claim 12, wherein the barrier device is transparent to ultraviolet light, and wherein the method further comprises passing ultraviolet light through the barrier device.

14. The method according to claim 1, further comprising delivering a therapeutic agent to the cavity via a therapeutic agent delivery tube.

15. The method according to claim 14, wherein:
    the barrier device is shaped to define an opening therethrough,
    the therapeutic agent delivery tube is coupled to the barrier device such that a lumen of the therapeutic agent delivery tube lumen is in fluid communication with the opening, and
    delivering the therapeutic agent comprises delivering the therapeutic agent through the opening.

16. The method according to claim 1, wherein deploying the barrier device comprises deploying the barrier device such that an angle between (a) a longitudinal axis of the delivery tube, and (b) a normal to a plane defined by the barrier device upon deployment thereof from the delivery tube, is greater than 5 degrees.

17. The method according to claim 3, further comprising using a temperature sensor to sense a temperature of the cavity and communicate the sensed temperature to the temperature regulator, wherein regulating the temperature of the cavity comprises regulating the temperature in response to the sensed temperature.

18. A method for treating a cavity in a human body using a barrier device having a collapsed configuration and an expanded configuration, the method comprising:
    deploying the barrier device from a delivery tube, using a pushing element slidably disposed within a lumen of the delivery tube, the barrier device moving from the collapsed configuration to the expanded configuration upon being deployed; and
    conformingly contacting the barrier device with tissue surrounding the cavity, using a plurality of barrier-deployment elements coupled at respective distal ends thereof to the barrier device and to the pushing element,
    the cavity including a defect in bone tissue,
    wherein a first one of the barrier-deployment elements includes a spring, including:
        a first spring-arm that is pivotably coupled to the pushing element at a proximal end of the first spring-arm; and
        a second spring-arm that is pivotably coupled to the pushing element at a proximal end of the second spring-arm, wherein the proximal end of the second spring-arm is more longitudinally moveable with respect to the pushing element than is the proximal end of the first spring-arm.

19. A method for treating a cavity in a human body using a barrier device having a collapsed configuration and an expanded configuration, the method comprising:

deploying the barrier device from a delivery tube, using a pushing element slidably disposed within a lumen of the delivery tube, the barrier device moving from the collapsed configuration to the expanded configuration upon being deployed; and conformingly contacting the barrier device with tissue surrounding the cavity, using a plurality of barrier-deployment elements coupled at respective distal ends thereof to the barrier device and to the pushing element, the cavity including a defect in periodontal tissue, wherein a first one of the barrier-deployment elements includes a spring, including:
  a first spring-arm that is pivotably coupled to the pushing element at a proximal end of the first spring-arm; and
  a second spring-arm that is pivotably coupled to the pushing element at a proximal end of the second spring-arm, wherein the proximal end of the second spring-arm is more longitudinally moveable with respect to the pushing element than is the proximal end of the first spring-arm.

20. The method according to claim 1, wherein the second spring-arm is longer than the first spring-arm.

21. The method according to claim 1, wherein a distal portion of the pushing element is shaped to define a channel, and wherein the proximal end of the second spring-arm is longitudinally moveable within the channel.

22. The method according to claim 21, wherein the distal portion of the pushing element is shaped to define a hole, wherein the first spring-arm is coupled to the pushing element by the proximal end of the first spring-arm fitting in the hole, and wherein a length of the channel is greater than a diameter of the hole.

23. The method according to claim 1, wherein the barrier device is configured to move from the collapsed configuration to the expanded configuration at least by the proximal end of the second spring-arm moving in a proximal direction.

24. The method according to claim 1, wherein the first and the second spring-arms converge at respective distal ends thereof.

25. The method according to claim 1, wherein the proximal end of the second spring-arm is axially slidable with respect to the pushing element, and the proximal end of the first spring-arm is axially fixed with respect to the pushing element.

26. The method according to claim 1, wherein the barrier device includes a plurality of hinges, and wherein the first and the second spring-arms are hingedly coupled to the barrier device by exactly one of the hinges.

27. The method according to claim 4,
wherein the barrier device includes a plurality of hinges, which are distinct from the legs and are fixed to a proximal surface of the barrier device,
wherein the legs are hingedly coupled to the hinges, such that the legs are pivotable with respect to the hinges.

* * * * *